United States Patent [19]

Martel et al.

[11] 4,406,829

[45] Sep. 27, 1983

[54] NOVEL CYCLOPROPANE CARBOXYLATE ESTERS

[75] Inventors: Jacques Martel, Bondy; Jean Buendia, Le Perreux-sur-Marne; François Nezot, Thiais, all of France

[73] Assignee: Roussel Uclaf, Paris, France

[21] Appl. No.: 318,445

[22] Filed: Nov. 5, 1981

[30] Foreign Application Priority Data

Nov. 18, 1980 [FR] France ................................ 80 24407

[51] Int. Cl.³ ............................................ C07C 69/743

[52] U.S. Cl. ................................ 252/522 R; 560/118

[58] Field of Search ...................... 560/118; 252/522 R

[56] References Cited

U.S. PATENT DOCUMENTS

| | | | |
|---|---|---|---|
| 3,679,667 | 7/1972 | Fanta | 560/124 |
| 3,926,860 | 12/1975 | Chappell | 252/522 |
| 3,997,586 | 12/1976 | Martel | 560/118 |

FOREIGN PATENT DOCUMENTS

| | | | |
|---|---|---|---|
| 4022 | 9/1979 | European Pat. Off. | 560/118 |

*Primary Examiner*—Robert Gersil

*Attorney, Agent, or Firm*—Hammond & Littell, Weissenberger and Muserlian

[57] ABSTRACT

Novel esters of all possible isomers and mixtures thereof of compounds of the formula

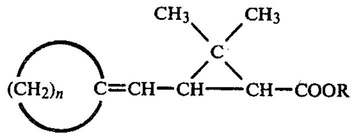

I wherein n is a number of 2,3 or 4 and R is selected from the group consisting of (a) alkyl of 1 to 12 carbon atoms optionally substituted with a member of the group consisting of cycloalkyl of 3 to 6 carbon atoms and a hydrocarbon chain of 2 to 8 carbon atoms optionally interrupted by an oxygen atom or a ketone group, (b) alkenyl and alkynyl of 3 to 8 carbon atoms, (c) cycloalkyl of 3 to 12 carbon atoms optionally containing at least one double bond and optionally substituted with at least one alkyl of 1 to 5 carbon atoms and (d) aralkyl of 7 to 12 carbon atoms optionally substituted with at least one member of the group consisting of alkyl of 1 to 4 carbon atoms, alkoxy of 1 to 4 carbon atoms, halogen and $-CF_3$ having perfume and insecticidal properties.

5 Claims, No Drawings

NOVEL CYCLOPROPANE CARBOXYLATE ESTERS

STATE OF THE ART

Commonly assigned U.S. patent application Ser. No. 307,629 filed 10/1/81 now abandoned describes cyclopropane carboxylic acid esters having in the 3-position an alkenyl group having perfume properties.

OBJECTS OF THE INVENTION

It is an object of the invention to provide the novel compounds of the formula I in their various isomeric forms and mixtures thereof and a process for their preparation.

It is another object of the invention to provide novel odorant compositions and to a novel method of imparting a pleasant odor to a composition by incorporating into the composition an odorantly effective amount of at least one compound of formula I.

These and other objects and advantages of the invention will become obvious from the following detailed description.

THE INVENTION

The novel compounds of the invention are compounds in all possible isomeric form and mixtures of the formula

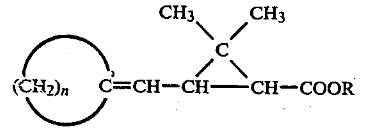
I wherein n is 2,3 or 4 and R is selected from the group consisting of (a) alkyl of 1 to 12 carbon atoms optionally substituted with cycloalkyl of 3 to 6 carbon atoms or a hydrocarbon of 2 to 8 carbon atoms optionally interrupted by an oxygen or ketone, (b) alkenyl and alkynyl of 3 to 8 carbon atoms, (c) cycloalkyl of 3 to 12 carbon atoms optionally containing at least one double bond and substituted with at least one alkyl and (d) aralkyl of 7 to 12 carbon atoms optionally substituted with at least one member of the group consisting of alkyl of 1 to 4 carbon atoms, alkoxy of 1 to 4 carbon atoms, halogen and $-CF_3$.

The compounds of formula I can exist in a number of possible isomeric forms as they possess two asymetric carbon atoms in the 1- and 3-positions of the cyclopropane ring and may also possess one or more asymetric centers or axes in the R portion of the molecule.

Examples of R are alkyl such a methyl, ethyl, n-propyl, isopropyl, butyl, tert.-butyl, isobutyl, n-pentyl, n-hexyl, n-heptyl, 2-methyl-pentyl, 2,3-dimethyl-butyl, 2-methyl-hexyl, 2,2-dimethyl-pentyl, 3,3-dimethyl-pentyl, 3-ethyl-pentyl, n-octyl, 2,2-dimethylhexyl, 3,3-dimethylhexyl, 3-methyl-3-ethyl-pentyl, nonyl, 2,4-dimethyl-heptyl and n-decyl; alkyl substituted with cycloalkyl or an hydrocarbon chain such as alkyl substituted with cyclopropyl, cyclopentyl, cyclohexyl, cyclohexenyl or cyclopentenyl; alkenyl such as butenyl, isobutenyl and crotonyl; alkynyl such as butynyl and propynyl; optionally unsaturated cycloalkyl such as cyclopropyl, cyclopentyl, cyclohexyl, cycloheptyl and cyclooctyl containing several double bonds and preferably 2 double bonds or substituted with at least one alkyl of 1 to 3 carbon atoms such as methyl, ethyl and n-propyl.

R may also be aralkyl such as benzyl or phenethyl optionally substituted in the m-, p- and/or o-positions with at least one member of the group consisting of alkyl and alkoxy of 1 to 4 carbon atoms such as methyl or methoxy, $-CF_3$ or a halogen such as chlorine or fluorine.

Preferred compounds of formula I are those wherein R is alkyl of 1 to 4 carbon atoms and those wherein n is 3 or 4.

Specific preferred compounds of formula I are isopropyl (1R,trans) 2,2-dimethyl-3-cyclobutylidenemethyl-cyclopropane-1-carboxylate, isopropyl (1R,cis) 2,2-dimethyl-3-cyclobutylidenemethyl-cyclopropane-1-carboxylate and methyl (1R,trans) 2,2-dimethyl-3-cyclobutylidenemethyl-cyclopropane-1-carboxylate.

The novel process of the invention for the preparation of the compounds of formula I comprises reacting an acid of the formula

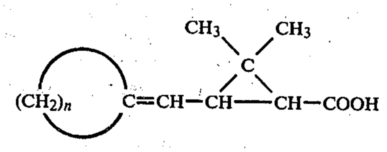
II or a functional derivative thereof wherein n has the above definition with an alcohol of the formula

R—OH III or a functional derivative thereof wherein R has the above definition to obtain the corresponding compound of formula I.

The functional derivative of the acid of formula II is the acid chloride or acid anhydride, preferably by reacting the acid chloride and the alcohol of formula III although other classical methods for the formation of esters are equally useful.

The novel odorant compositions of the invention are comprised of an odorantly effective amount of at least one compound of formula I and a carrier. The compositions have an agreeable odor such as a floral odor, a flowerly odor, a fresh odor, a spice odor or a woody odor.

The compositions may be used as odorants in perfumes or to prepare odorant compositions which serve as perfume bases. They are also useful in the preparation of hygienic compositions such as soaps, talcum powders, shampoos, dentifrices, bath salts, bath oils or bubble baths, deodorants or in the preparation of cosmetic products such as cremes, makeup milks, lotions, face paint, lipsticks and nail polishes. The compositions may also be used in detergent compositions such as washing powders or the preparation of maintenance products such as waxes or the preparation of insecticides.

The compounds of formula I may be used to impart a pleasant odor to products lacking any odor or to raise up, exalt or modify the odor of compositions having their own odor. They may also be used to mask a disagreeable odor of a product. Naturally, the perfumes, hygienic products, cosmetics, detergent products and maintenance products are prepared by the usual techniques employed in these industries which are largely described in the literature.

The compositions of the invention may contain other usual ingredients such as support vehicles, modifiers, fixing agents, preservatives, stabilizers and other ingredients such as supports, solvents, dispersants and emulsifiers usually used.

When the compounds of formula I are used in perfumes, a small amount of the compounds of formula I is added to other components well known in the perfumery art which may be natural products such as vetiver essence, cedar essence, bergamot orange essence, pine needle essence, lemon essence, jasmin or mandarin orange essence or may be synthetic products such as aldehydes commonly used in perfumery such as hydroxy-citronella, ketones such as $\alpha$-ionone, phenolic compounds such as eugenol, alcohols such as geraniol or lactones such as coumarine.

The amounts of the compounds of formula I used in perfumes will vary greatly as a function of the nature of the specific compound, the use one wishes to make, the intensity of the odor desired as well as, naturally, the nature and composition of the other ingredients added thereto. In perfumes, there may be used 0.1 to 10 parts by weight of the compounds of formula I per 100 parts by weight of the compositions and when used in a perfume base, the base may contain up to 20% by weight of the compound of formula I. When used in detergents, 0.1 to 2 parts by weight of the compounds of formula I per 100 parts by weight of the detergent composition may be used.

The normal method of the invention for imparting a pleasant odor to a composition comprises incorporating into a composition an odorantly effective amount of at least one compound of formula I.

In the following examples there are described several preferred embodiments to illustrate the invention. However, it is to be understood that the invention is not intended to be limited to the specific embodiments.

EXAMPLE 1

Isopropyl (1R,trans) 2,2-dimethyl-3-cyclobutylidenemethyl-cyclopropane-1-carboxylate A mixture of 12 g of (1R,trans) 2,2-dimethyl-3-cyclobutylidenemethyl-cyclopropane-1-carboxylic acid chloride in 25 ml of isopropanol was stirred for 8 hours and was distilled to dryness at 45° C. under reduced pressure. The residue was taken up in isopropyl ether and the solution was washed with water, dried and evaporated to dryness under reduced pressure at 45° C. The residue was chromatographed over silica gel and was eluted with a 9-1 petroleum ether (b.p.=60°-80° C.)-isopropyl ether mixture to recover the fraction with an Rf=0.35. The solvent was evaporated under reduced pressure to obtain 7.8 g of isopropyl (1R,trans) 2,2-dimethyl-3-cyclobutylidenemethyl-cyclopropane-1-carboxylate with a boiling point of 64°-66° C. at 0.1 mm Hg and a specific rotation of $[\alpha]_D^{20}=-24.5°$ (c=2% in chloroform).

EXAMPLE 2

Isopropyl (1R,cis) 2,2-dimethyl-3-cyclobutylidenemethyl-cyclopropane-1-carboxylate 8 g of (1R,cis) 2,2-dimethyl-3-cyclobutylidenemethyl-cyclopropane-1-carboxylic acid chloride and 10 ml of benzene were added at 10° C. to a solution of 50 ml of benzene, 4 g of isopropanol and 4 g of pyridine and the reaction mixture was stirred for 8 hours. The mixture was poured into iced water and the decanted organic phase was washed with water, with aqueous sodium bicarbonate solution, with water, with N hydrochloric acid and finally with water. The solution was dried and evaporated to dryness under reduced pressure at 45° C. The residue was chromatographed over silica gel and was eluted with an 8-2 petroleum ether (b.p.=60°-80° C.)-isopropyl ether mixture to obtain the fraction with an Rf=0.55. The solution was evaporated to dryness under reduced pressure at 45° C. to obtain 5 g of isopropyl (1R,cis) 2,2-dimethyl-3-cyclobutylidenemethyl-cyclopropane-1-carboxylate with a boiling point of 66°~68° C. at 0.1 mm Hg and a specific rotation of $[\alpha]_D^{20}=+74.5°$ (c=1% in chloroform).

EXAMPLE 3

Methyl (1R,trans) 2,2-dimethyl-3-cyclobutylidenemethyl-cyclopropane-1-carboxylate 100 ml of a solution of 20% butyllithium in cyclohexane were added at 30° C. to a mixture of 110 g of cyclobutyl triphenylphosphine bromide in 550 ml of dimethoxyethane and then 23 g of bicaronal and 150 ml of dimethoxyethane were added to the mixture. The mixture was refluxed for 4 hours and was held overnight at 20° C. and evaporated to dryness under reduced pressure at 50° C. The residue was taken up in water and the aqueous phase was extracted with isopropyl ether. The organic phase was washed with water, dried and evaporated to dryness under reduced pressure at 45° C. The residue was chromatographed over silica gel and was eluted with a 9-1 petroleum ether (b.p.=60°-80° C.)-isopropyl ether mixture to obtain 17 g of methyl (1R,trans) 2,2-dimethyl-3-cyclobutylidenemethyl-cyclopropane-1-carboxylate with a specific rotation of $[\alpha]_D^{20}=-9.5°$ (c=1% in chloroform).

EXAMPLE 4

Methyl (1R,cis) 2,2-dimethyl-3-cyclobutylidenemethyl-cyclopropane-1-carboxylate A mixture of 30 g of (1R,cis) 2,2-dimethyl-3-cyclobutylidenemethyl-cyclopropane-1-carboxylic acid chloride and 50 ml of benzene was added to a solution of 15 g of methanol, 15 g of pyridine and 200 ml of benzene and the mixture was stirred at 20° C. for 8 hours and was then poured into iced water. The decanted organic phase was washed with water, with a sodium bicarbonate solution, with water, with dilute hydrochloric acid and finally with water. The organic phase was dried and evaporated to dryness under reduced pressure at 45° C. The residue was chromatographed over silica gel and was eluted with an 8-2 petroleum ether (b.p.=60°-80° C.)-isopropyl ether mixture to recover the fraction with an Rf=0.5. The solvent was distilled off under reduced pressure at 45° C. and the residue was rectified under reduced pressure to obtain 23 g of methyl (1R,cis) 2,2-dimethyl-3-cyclobutylidenemethyl-cyclopropane-1-carboxylate with a boiling point of 63°-64° C. at 0.1 mm Hg and a specific rotation of $[\alpha]_D^{20}=+119°$ (c=1.5% in chloroform).

EXAMPLE 5

Methyl (1R,cis) 2,2-dimethyl-3-cyclopentylidenemethyl-cyclopropane-1-carboxylate 3.5 g of methyl N,N'-diisopropyl-carbamimate were added to a solution of 3.9 g of (1R,cis) 2,2-dimethyl-3-cyclopentylidenemethyl-cyclopropane-1-carboxylic acid in 20 ml of ethyl acetate and the mixture was refluxed for 2 hours and filtered. The filtrate was evaporated to dryness and the 6.2 g of residue were chromatographed over silica gel. Elution with a 98-2 petroleum ether (b.p.=40°-70° C.)—isopropyl ether mixture yielded 1.3 g of methyl (1R,cis) 2,2-dimethyl-3-cyclopentylidenemethyl-cyclopropane-1-carboxylate with a specific rotation of $[\alpha]_D^{20}=+93°\pm2°$ (c=1% in ethanol).

EXAMPLE 6

Ethyl (1R,cis) 2,2-dimethyl-3-cyclopentylidenemethyl-cyclopropane-1-carboxylate 7.5 g of ethyl N,N'-diisopropyl-carbamimidate were added to a solution of 7.8 g of (1R,cis) 2,2-dimethyl-3-cyclopentylidenemethyl-cyclopropane-1-carboxylic acid in 20 ml of ethyl acetate and the mixture was refluxed for 2 hours and was filtered. The filtrate was evaporated to dryness and the 13 g of residue were chromatographed over silica gel. Elution with a 7-3 cyclohexane-ethyl acetate mixture and the fraction with a Rf=0.45 was evaporated to dryness under reduced pressure to obtain 1.4 g of ethyl (1R,cis) 2,2-dimethyl-3-cyclopentylidenemethyl-cyclopropane-1-carboxylate with a specific rotation of $[\alpha]_D^{20}=+76°\pm2°$ (c=1% in ethanol).

EXAMPLE 7

Isopropyl (1R,cis) 2,2-dimethyl-3-cyclopentylidenemethyl-cyclopropane-1-carboxylate 5 ml of isopropyl N,N'-diisopropyl carbamimidate were added to a solution of 3.9 g of (1R,cis) 2,2-dimethyl-3-cyclopentylidenemethyl-cyclopropane-1-carboxylic cid in 20 ml of ethyl acetate and the mixture refluxed for 2 hours and was filtered. The filtrate was evaporated to dryness and the 7.3 g of residue were chromatographed over silica gel. Elution with a 7-3 cyclohexane-ethyl-acetate mixture yielded 1.9 g of isopropyl (1R,cis) 2,2-dimethyl-3-cyclopentylidenemethyl-cyclopropane-1-carboxylate with a specific rotation of $[\alpha]_D^{20}=+50.5°\pm1.5°$ (c=1.5% in benzene) and $+61°\pm2°$ (c=0.8% in ethanol).

EXAMPLE 8

Ethyl (1R,trans) 2,2-dimethyl-3-cyclobutylidenemethyl-cyclopropane-1-carboxylate A solution of 12 g of (1R,trans) 2,2-dimethyl-3-cyclobutylidenemethyl-cyclopropane-1-carboxylic acid chloride and 25 ml of ethanol was stirred at room temperature for 8 hours and was evaporated to dryness at 45° C. under reduced pressure. The residue was taken up in isopropyl ether and the solution was washed with water, dried and evaporated to dryness under reduced pressure at 45° C. The residue was chromatographed over silica gel and was eluted with a 9-1 petroleum ether (b.p.=60°-80° C.)—isopropyl ether mixture. The fraction with an Rf=0.35 was evaporated to dryness under reduced pressure at 45° C. and the product was rectified to obtain 8 g of ethyl (1R,trans) 2,2-dimethyl-3-cyclobutylidenemethyl-cyclopropane-1-carboxylate with a boiling point of 78°-79° C. at 0.1 mm Hg and a specific rotation of $[\alpha]_D^{20}=-18°$ (c=2% in chloroform).

EXAMPLE 9

Using the procedure of Example 1, (1R,trans) 2,2-dimethyl-3-cyclobutylidenemethyl-cyclopropane-1-carboxylic acid and 3-buten-1-ol were reacted to obtain 3-buten-1-yl (1R,trans) 2,2-dimethyl-3-cyclobutylidenemethyl-cyclopropane-1-carboxylate.

EXAMPLE 10

Using the procedure of Example 1, (1R,cis) 2,2-dimethyl-3-cyclobutylidenemethyl-cyclopropane-1-carboxylic acid and 3-buten-1-ol were reacted to obtain 3-buten-1-yl (1R,cis) 2,2-dimethyl-3-cyclobutylidenemethyl-cyclopropane-1-carboxylate.

EXAMPLE 11

Using the procedure of Example 1, (1R,cis) 2,2-dimethyl-3-cyclobutylidenemethyl-cyclopropane-1-carboxylic acid and 2-phenethanol were reacted to obtain 2-phenethyl (1R,cis) 2,2-dimethyl-3-cyclobutylidenemethyl-cyclopropane-1-carboxylate.

EXAMPLE 12

| Product of Example | Odor given Off |
|---|---|
| 1 | woody note, rose, rustic, grape woody type acetal |
| 2 | rose note, metallic |
| 3 | rose note, lemony |

EXAMPLE 13

A "rose" composition was prepared containing the following ingredients (parts by weight): 100 parts of the product of Example 1, 15 parts of α Ionone, 15 parts of Aldehyde C 9 I/10 PDG, 15 parts of musk ketone, 30 parts of Benjoin resinoid, 40 parts of citronella acetate, 60 parts of bourbon Rhodine, 170 parts of phenethanol, 15 parts of methylionone, 15 parts of Nerol, 45 parts of geranyl acetate, 300 parts of citronellal and 180 parts of terpene-free geranium.

EXAMPLE 14

A toilet soap was prepared containing 5 parts by weight of the product of Example 3 and 1,000 parts by weight of a commercial soap paste. A commercial powdered detergent was also prepared containing 1 part of the product of Example 2 per 1,000 parts of the detergents.

Various modifications of the products and process of the invention may be made without departing from the spirit or scope thereof and it is to be understood that the invention is intended to be limited only as defined in the appended claims.

What we claim is:

1. A method of imparting a pleasant odor to a composition comprising incorporating into the composition an odorantly effective amount of at least one compound in all its possible isomeric forms and mixtures thereof of the formula

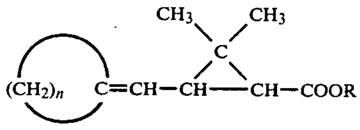

wherein n is 2,3 or 4 and R is selected from the group consisting of (a) alkyl of 1 to 12 carbon atoms optionally substituted with cycloalkyl of 3 to 6 carbon atoms or a hydrocarbon of 2 to 8 carbon atoms optionally interrupted by an oxygen or ketone, (b) alkenyl and alkynyl of 3 to 8 carbon atoms (c) cycloalkyl of 3 to 12 carbon atoms optionally containing at least one double bond and substituted with at least one alkyl and (d) aralkyl of 7 to 12 carbon atoms optionally substituted with at least one member of the group consisting of alkyl of 1 to 4 carbon atoms, alkoxy of 1 to 4 carbon atoms, halogen and $-CF_3$.

2. A method of claim 1 wherein R is alkyl of 1 to 4 carbon atoms.

3. A method of claim 1 wherein n is 3 or 4.

4. A method of claim 1 wherein the acid moiety has the 1R,cis or 1R, trans structure.

5. A method of claim 1 wherein the compound is selected from the group consisting of isopropyl (1R,trans) 2,2-dimethyl-3-cyclobutylidenemethyl-cyclopropane-1-carboxylate, isopropyl (1R,cis) 2,2-dimethyl-3-cyclobutylidenemethyl-cyclopropane-1-carboxylate and methyl (1R,trans) 2,2-dimethyl-3-cyclobutylidenemethyl-cyclopropane-1-carboxylate.

* * * * *